United States Patent
Candau et al.

(10) Patent No.: US 6,416,748 B1
(45) Date of Patent: Jul. 9, 2002

(54) EMULSIFIER-FREE UV-PHOTOPROTECTING EMULSIONS COMPRISING MICRONIZED INSOLUBLE SCREENING AGENTS

(75) Inventors: Didier Candau, Bievres; Anne-Marie Pisson, Boussy St Antoine, both of (FR)

(73) Assignee: Societe L'Oreal, Paris (FR)

( * ) Notice: Subject to any disclaimer, the term of this patent is extended or adjusted under 35 U.S.C. 154(b) by 0 days.

(21) Appl. No.: 09/693,894

(22) Filed: Oct. 23, 2000

(30) Foreign Application Priority Data

Oct. 22, 1999 (FR) .............................. 99 13221

(51) Int. Cl.⁷ .......................... A61K 7/42; A61K 7/44; A61K 7/00; A61K 3/53
(52) U.S. Cl. .......................... 424/59; 424/60; 424/400; 424/401; 514/241
(58) Field of Search .......................... 424/59, 60, 400, 424/401; 514/241

(56) References Cited

U.S. PATENT DOCUMENTS 5,980,872 A   11/1999   Luther et al. .................. 424/59

FOREIGN PATENT DOCUMENTS

| EP | 0 987 006 A2 | 3/2000 |
| JP | 06279252 | 10/1994 |
| WO | WO 97/03643 | 2/1997 |

*Primary Examiner*—Shelley A. Dodson
(74) *Attorney, Agent, or Firm*—Burns, Doane, Swecker & Mathis, L.L.P.

(57) ABSTRACT

Topically applicable, water-resistant but emulsifier-free cosmetic/dermatological emulsions well suited for the UV-photoprotection of human skin and/or hair contain (a) at least one aqueous phase and (b) at least one fatty phase, (c) an effective UV-photoprotecting amount of at least one micronized organic UV-screening agent insoluble therein, the mean particle size of such micronized particles ranging from 0.01 to 2 $\mu$m and (d) optionally, at least one crosslinked polymer of at least one ethylenically unsaturated monomer.

53 Claims, No Drawings

EMULSIFIER-FREE UV-PHOTOPROTECTING EMULSIONS COMPRISING MICRONIZED INSOLUBLE SCREENING AGENTS

CROSS-REFERENCE TO PRIORITY APPLICATION

This application claims priority under 35 U.S.C. §119 of FR-99/13221, filed Oct. 22, 1999, hereby expressly incorporated by reference.

CROSS-REFERENCE TO COMPANION APPLICATIONS

Copending applications Ser. Nos. 09/693,888 09/693,339, and 09/693,887, each assigned to the assignee hereof, each filed concurrently herewith and each also hereby expressly incorporated by reference.

BACKGROUND OF THE INVENTION

1. Technical Field of the Invention

The present invention relates to novel cosmetic/dermatological emulsions devoid of emulsifier, comprising:

(a) at least one aqueous phase and (b) at least one fatty phase;

(c) at least one photoprotective system or agent suited for screening out UV-irradiation, containing at least one organic UV-screening agent insoluble in such emulsions.

The present invention also relates to cosmetic/dermatological compositions suited for the photoprotection of the skin or of the hair.

2. Description of the Prior Art

It is known to this art that light radiation of wavelengths of from 280 nm to 400 nm permits tanning of the human epidermis, and that radiation of wavelengths more particularly of from 280 nm to 320 nm, i.e., UV-B radiation, causes erythemas and skin burns which can hinder the development of natural tanning.

For these reasons as well as for aesthetic reasons, there is a constant demand to control this natural tanning such as to thereby control the color of the skin; it is therefore advisable to screen out UV-B radiation.

It is also known to this art that UV-A radiation of wavelengths of from 320 nm to 400 nm, which promotes tanning of the skin, also is capable of causing damage thereto, in particular in the case of a sensitive skin or of a skin continually exposed to solar radiation. UV-A radiation, causes, in particular, loss of elasticity of the skin and the appearance of wrinkles which promotes premature skin aging. UV-A radiation promotes the onset of the erythema reaction or amplifies this reaction in certain individuals and may even be responsible for phototoxic or photoallergic reactions. Thus, for aesthetic and cosmetic reasons such as the preservation of the natural elasticity of the skin for example, an increasing number of individuals seek to control the effect of UV-A radiation on their skin. It is therefore desirable to also screen out UV-A radiation.

A wide variety of cosmetic compositions intended for the photoprotection (UV-A and/or UV-B) of the skin are also known to this art.

These anti-sun or sunscreen compositions are quite often provided in the form of an emulsion, of the oil-in-water (O/W) type (namely, a cosmetically and/or dermatologically acceptable carrier comprising an aqueous dispersing continuous phase and a fatty dispersed discontinuous phase) or of the water-in-oil (W/O) type (dispersed aqueous phase in a continuous fatty phase), which contains, at various concentrations, one or more lipophilic conventional organic UV-screening agents and/or inorganic nanopigments of metal oxides, which are suited for selectively absorbing the harmful UV radiation, these screening agents (and the quantities thereof) being selected according to the desired sun protection factor (the sun protection factor (SPF) being mathematically expressed by the ratio of the irradiation time required to attain the erythematogenic threshold with the UV-screening agent to the time required to attain the erythematogenic threshold in the absence of UV-screening agent). In such emulsions, the hydrophilic screening agents are present in the aqueous phase and the lipophilic screening agents are present in the fatty phase.

The oil-in-water emulsions are, in general, more accepted by the consumer than the water-in-oil emulsions because, in particular, of their pleasant feel (similar to water) and their presentation in the form of a non-oily cream or milk; however, they also more readily lose their UV protection efficacy as soon as they come into contact with water. Indeed, the hydrophilic screening agents tend to disappear in water, upon washing in the sea or in a swimming pool, under the shower or when engaged in water sports; thus, anti-sun or sunscreen compositions containing same, whether alone or combined with lipophilic screening agents, no longer provide the desired initial protection as soon as the substrate (skin or hair) to which they have been applied is contacted with water.

Anti-sun (sunscreen) compositions exhibiting improved resistance to water have been formulated as water-in-oil emulsions. Indeed, a hydrophilic screening agent is more stable to water in a water-in-oil emulsion than in an oil-in-water emulsion. However, as indicated above, such compositions are not yet completely satisfactory since they promote, after application, a fat-like impression which is particularly unpleasant for the user.

Thus, serious need continues to exist for anti-sun or sunscreen compositions which impart to the skin and/or the hair effective solar protection which is stable over time and resistant to water (stability to water) and the cosmetic performance of which presents features that would be comparable to those obtained with conventional oil/water emulsions.

SUMMARY OF THE INVENTION

It has now surprisingly and unexpectedly been determined that specific emulsions containing at least one organic UV-screening agent insoluble in micronized form in the different phases of these emulsions and typically at least one crosslinked polymer, but containing no emulsifier, not only provide anti-sun compositions whose cosmetic performance features are comparable to those generally associated with a conventional sunscreen composition formulated as an oil/water emulsion, but also exhibit good stability as well as enhanced stability to water.

These discoveries constitute the basis of the present invention.

Briefly, the present invention features cosmetic/dermatological emulsions devoid of emulsifying agent but comprising (a) at least one aqueous phase and (b) at least one fatty phase, and (c) at least one photoprotective system or agent adopted for screening out UV radiation, containing at least one organic UV-screening agent insoluble in such emulsions, in micronized form, in which the mean size of the particles ranges from 0.01 $\mu$m to 2 $\mu$m.

DETAILED DESCRIPTION OF BEST MODE AND SPECIFIC/PREFERRED EMBODIMENTS OF THE INVENTION

More particularly according to the present invention, by "cosmetic or dermatological emulsion" is intended any emulsion in which the aqueous phase and the fatty phase contain substances or substrates which are cosmetically or dermatologically acceptable for topical application onto human keratinous materials including the skin, the hair, the eyelashes, the eyebrows, the lips, the nails or the mucous membranes.

By "emulsion without (or devoid of) emulsifier" or "emulsifier-free" is intended any oil-in-water emulsion (comprising an aqueous dispersing continuous phase and a fatty dispersed discontinuous phase) or any water-in-oil emulsion (comprising a fatty dispersing continuous phase and an aqueous dispersed discontinuous phase) containing no conventional emulsifying surfactant.

By "insoluble organic UV-screening agent" is intended according to the present invention organic UV-screening agents which are insoluble in the cosmetic media generally included in anti-sun formulations and more particularly whose solubility in water at 25° C. is less than 0.1% by weight and whose solubility in paraffin oil at 25° C. is less than 1% by weight.

By "photoprotective system suited for screening out UV radiation" is intended any system including one or more organic compounds and/or inorganic compounds screening out UV-A and/or UV-B radiation.

The present invention thus features formulating the subject emulsifier-free emulsions into cosmetic compositions for the protection of the skin and/or of the hair against ultraviolet radiation, in particular solar radiation.

The insoluble organic screening agents according to the invention are provided in micronized form. The mean or average size of the particles ranges from 0.01 $\mu$m to 2 $\mu$m and more preferably from 0.02 $\mu$m to 1.5 $\mu$m and even more preferably from 0.05 $\mu$m to 1.0 $\mu$m.

The insoluble organic screening agents according to the invention may be provided in the desired particulate form by any appropriate means such as, in particular, grinding in the dry state or in solvent medium, sieving, spray-drying, micronization or spraying.

The insoluble organic screening agents according to the invention in micronized form may, in particular, be provided by a method of grinding an insoluble UV-screening agent in the form of particles having a coarse size in the presence of an appropriate surfactant which makes it possible to enhance the dispersion of the particles thus obtained in the cosmetic formulations.

One embodiment of a method of micronization of insoluble organic screening agents is described in GB-A-2,303,549 and EP-A-893119 incorporated by reference herein. The grinding apparatus according to the invention may be a jet mill, a ball mill, a vibratory mill or a hammer mill and preferably a mill featuring high-speed agitation or an impact mill and more particularly a rotating ball mill, a vibratory mill, a tube mill or a rod mill.

According to this particular methodology, the alkyl polyglucosides having the structure $C_nH_{2n+1}O(C_6H_{10}O_5)_xH$ in which n is an integer from 8 to 16 and x is the average degree of polymerization of the structural unit ($C_6H_{10}O_5$) and ranges from 1.4 to 1.6, are included as surfactants for the grinding of the screening agents. They are advantageously selected from among $C_1$–$C_{12}$ esters of a compound having the structure $C_nH_{2n+1}O(C_6H_{10}O_5)_xH$ and more precisely an ester prepared by reacting a $C_1$–$C_{12}$ carboxylic acid such as formic, acetic, propionic, butyric, sulfosuccinic, citric or tartaric acid with one or more free OH functions on the glucoside unit ($C_6H_{10}O_5$). Such surfactants are typically employed at a concentration ranging from 1% to 50% by weight and more preferably from 5% to 40% by weight relative to the insoluble screening agent in its micronized form.

The emulsions without or devoid of emulsifier according to the present invention typically comprise at least one crosslinked polymer of at least one ethylenically unsaturated monomer.

Exemplary crosslinked polymers of at least one ethylenically unsaturated monomer according to the invention include, in particular:

(i) the crosslinked homopolymers or copolymers of at least one ethylenically unsaturated monomer having a sulfonic functional group, in free or partially or completely salified form;

(ii) the crosslinked copolymers of at least one ethylenically unsaturated monomer having a carboxylic acid functional group, in free or partially or completely salified form, or of an ester or amide derivative thereof;

(iii) the crosslinked homopolymers or copolymers of at least one cationic ethylenically unsaturated monomer of the ester or amide type.

The monomers having a sulfonic acid function are selected, in particular, from among 2-acrylamido-2-methylpropanesulfonic acid as well as the salts thereof.

The monomers having a carboxylic acid function are selected, in particular, from among acrylic acid and methacrylic acid as well as the salts thereof. Their esters are advantageously selected from among those of (meth)acrylic acid and $C_1$–$C_{30}$ alcohols. Their amides are advantageously selected from among those of (meth)acrylic acid and $C_1$–$C_{30}$ amines and, more particularly, methacrylamide and/or acrylamide.

The cationic monomers of the ester or amide type are preferably selected from among ammonium (meth)acrylate, dialkylaminoalkyl (meth)acrylates, in particular dimethylaminoethyl methacrylate; dialkylaminoalkyl (meth)acrylamides as well as their quaternary salts or acids; the alkyl radicals preferably being $C_1$–$C_4$.

The crosslinked polymers of the invention comprise the polymerizates of at least one ethylenically unsaturated crosslinking agent which is preferably selected from among divinylbenzene; tetraallyloxyethane; diallyl ether; polyallyl polyglyceryl ethers; allyl ethers of alcohols of the sugar series such as erythritol, pentaerythritol, arabitol, sorbitol or glucose; methylenebisacrylamide, ethylene glycol di(methyl)acrylate, di(meth)acrylamide, cyanomethyl acrylate, vinyloxyethyl (meth)acrylate and their metal salts.

Exemplary crosslinked homopolymers or copolymers of at least one ethylenically unsaturated monomer having a sulfonic function, which are at least 90% neutralized, more particularly include the crosslinked homopolymers of 2-acrylamido-2-methylpropanesulfonic acid, which are at least 90% neutralized, such as those described in EP-A-0,815,828 (hereby expressly incorporated by reference), the crosslinked copolymers of 2-acrylamido-2-methylpropanesulfonic acid and of acrylamide which are partially or completely neutralized (with a base such as sodium hydroxide, potassium hydroxide or an amine) as described in EP-A-0,503,853 (also expressly incorporated by reference) and more particularly in Example 1 thereof.

Exemplary crosslinked copolymers of at least one ethylenically unsaturated monomer having a carboxylic acid function or of an ester or amide derivative thereof, more particularly include the non-ionic or anionic amphiphilic polymers comprising at least one fatty chain or substituent and at least one hydrophilic structural unit.

The non-ionic amphiphilic polymers are advantageously selected from among:

(i) the copolymers of $C_1$–$C_6$ alkyl methacrylates or acrylates and of amphiphilic monomers comprising at least one fatty chain such as, for example, the oxyethylenated stearyl acrylate/methyl acrylate copolymer marketed by Goldschmidt under the trademark ANTIL 208;

(ii) the copolymers of hydrophilic methacrylates or acrylates and of hydrophobic monomers comprising at least one fatty chain such as, for example, the polyethylene glycol methacrylate/lauryl methacrylate copolymer.

The anionic amphiphilic polymers are advantageously selected from among those in which the hydrophilic structural unit is an ethylenically unsaturated anionic monomer, more particularly of a vinylcarboxylic acid and most particularly of an acrylic acid, a methacrylic acid or mixture thereof, and also comprising an allyl ether structural unit containing a fatty chain which corresponds to a monomer having the following formula (I):

$$CH_2=C(R')CH_2OB_nR \qquad (I)$$

in which R' is H or $CH_3$, B represents the ethyleneoxy radical, n is zero or an integer ranging from 1 to 100, R is a hydrocarbon radical selected from among alkyl, arylalkyl, aryl, alkylaryl or cycloalkyl radicals, having from 8 to 30 carbon atoms, preferably 10 to 24, and more preferably from 12 to 18 carbon atoms. A more particularly preferred structural unit of formula (I) is a structural unit in which R' is H, n is equal to 10, and R is a stearyl ($C_{18}$) radical. Anionic amphiphilic polymers of this category are described and prepared, via technique for polymerization in emulsion, in EP-0,216,479 B2.

Exemplary of these associative anionic polymers are those polymers prepared from 20% to 60% by weight of acrylic acid and/or of methacrylic acid, from 5% to 60% by weight of lower alkyl(meth)acrylates, from 2% to 50% by weight of allyl ether bearing a fatty chain substituent of formula (I), and from 0% to 1% by weight of a crosslinking agent which is a well known copolymerizable polyethylenic unsaturated monomer such as diallyl phthalate, allyl (meth)acrylate, divinylbenzene, (poly)ethylene glycol dimethacrylate and methylenebisacrylamide. There are most particularly preferred according to the invention.

Among the latter, the crosslinked terpolymers of methacrylic acid, ethyl acrylate, polyethylene glycol (10 EO) stearyl alcohol ether (Steareth 10), in particular those marketed by Allied Colloids, under the trademarks SALCARE SC 80 and SALCARE SC 90 which are aqueous emulsions containing 30% of a crosslinked terpolymer of methacrylic acid, of ethyl acrylate and of steareth-10-allyl ether (40/50/10) are most particularly preferred.

Exemplary associative anionic polymers include those anionic polymers comprising at least one hydrophilic structural unit of the olefinic unsaturated carboxylic acid type, and at least one hydrophobic structural unit exclusively of the $(C_{10}$–$C_{30})$alkyl ester of unsaturated carboxylic acid type.

Preferably, these polymers are selected from among those whose hydrophilic structural unit of the olefinic unsaturated carboxylic acid type corresponds to the monomer having the following formula (II):

(II)

in which $R_1$ is H or $CH_3$ or $C_2H_5$, namely, acrylic acid, methacrylic acid or ethacrylic acid structural units, and whose hydrophobic structural unit of the $(C_{10}$–$C_{30})$alkyl ester of unsaturated carboxylic acid type corresponds to the monomer having the following formula (III):

(III)

in which $R_2$ is H or $CH_3$ or $C_2H_5$ (namely, acrylate, methacrylate or ethacrylate structural units) and preferably H (acrylate units) or $CH_3$ (methacrylate units), and $R_3$ is a $C_{10}$–$C_{30}$, and preferably $C_{12}$–$C_{22}$, alkyl radical.

$(C_{10}$–$C_{30})$alkyl esters of unsaturated carboxylic acids in accordance with the invention include, for example, lauryl acrylate, stearyl acrylate, decyl acrylate, isodecyl acrylate and the corresponding methacrylates, lauryl methacrylate, stearyl methacrylate, decyl methacrylate and isodecyl methacrylate.

Anionic polymers of this type are for example described and prepared according to the methodology set forth in U.S. Pat. Nos. 3,915,921 and 4,509,949.

Exemplary of the above polymers are the products marketed by Goodrich under the trademark PEMULEN TR1, PEMULEN TR2, CARBOPOL 1382, and even more preferably PEMULEN TR1, and the product marketed by S.E.P.P.I.C. under the trademark COATEX SX. These are most particularly preferred according to the present invention.

Exemplary crosslinked homopolymers or copolymers of at least one cationic ethylenically unsaturated monomer of the ester or amide type, include, in particular:

(i) the homopolymers of ammonium acrylate or the copolymers of ammonium acrylate and of acrylamide, such as the product marketed under the trademark BOZEPOL C NOUVEAU or the product PAS 5193 marketed by Hoechst (described and prepared as set forth in FR-2,416,723, and U.S. Pat. Nos. 2,798,053 and 2,923,692);

(ii) the homopolymers of dimethylaminoethyl methacrylate quaternized with methyl chloride, such as the products marketed under the trademarks SALCARE 95 and SALCARE 96 by Allied Colloids, or the copolymers of dimethylaminoethyl methacrylate quaternized with methyl chloride and of acrylamide, such as the product SALCARE SC92 marketed by Allied Colloids or the product PAS 5194 marketed by Hoechst (described and prepared as set forth in EP-A-0,395,282).

The above polymers according to the invention are generally formulated into the subject anti-sun or sunscreen compositions in a concentration (expressed as active substance AS) ranging from 0.01% to 10% by weight, and preferably from 0.1% to 5% by weight, relative to the total weight of the composition.

The insoluble and micronized organic UV-screening agents in accordance with this invention may be selected, in particular, from among the organic UV-screening agents of the oxanilide type, of the triazine type, of the triazole type, of the vinylamide type and of the cinnamide type.

Exemplary UV-screening agents of the oxanilide type include those having the structural formula (1):

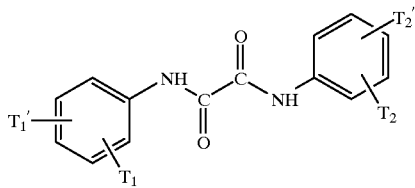

(1)

in which $T_1$, $T'_1$, $T_2$ and $T'_2$, which may be identical or different, are each a $C_1$–$C_8$ alkyl radical or a $C_1$–$C_8$ alkoxy radical. These compounds are described in WO-95/22,959.

Exemplary thereof are the commercial products TINU-VIN 315 and TINUVIN 312 marketed by Ciba-Geigy and respectively having the structural formulae:

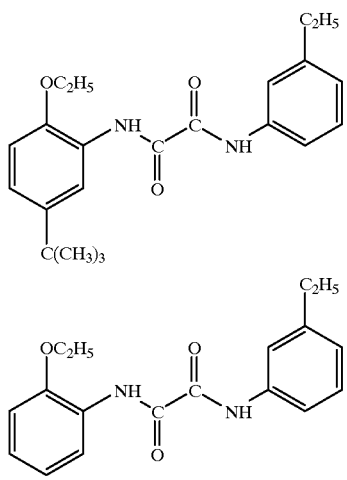

The preferred 1,3,5-triazine derivatives in accordance with the invention have the following structural formula (2):

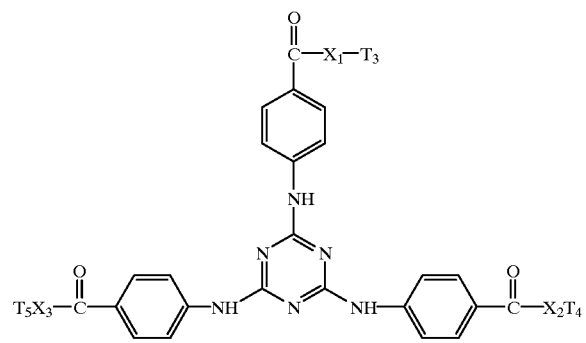

(2)

in which $X_1$, $X_2$ and $X_3$, which may be identical or different, are each an oxygen atom or a radical —NZ—; the radicals Z, which may be identical or different, are each hydrogen or a linear or branched $C_1$–$C_{18}$ alkyl radical, a $C_5$–$C_{12}$ cycloalkyl radical optionally substituted with one or more $C_1$–$C_4$ alkyl radicals; $T_3$, $T_4$ and $T_5$, which may be identical or different, are each hydrogen, an alkali metal, an ammonium radical which is optionally substituted with one or more alkyl or hydroxyalkyl radicals, a linear or branched $C_1$–$C_{18}$ alkyl radical, a $C_5$–$C_{12}$ cycloalkyl radical which is optionally substituted with one or more $C_1$–$C_4$ alkyl radicals, a polyoxyethylenated radical having from 1 to 6 ethylene oxide units and whose terminal OH group is methylated or a radical of the following formulae (3), (4) or (5):

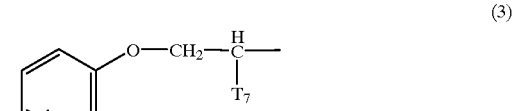

(3)

(4)

(5)

in which $T_6$ is hydrogen or a methyl radical; $T_7$ is a $C_1$–$C_9$ alkyl radical; p is an integer ranging from 0 to 3; q is an integer ranging from 1 to 10; A is a $C_4$–$C_8$ alkyl radical or a $C_5$–$C_8$ cycloalkyl radical; B is a linear or branched $C_1$–$C_8$ alkyl radical, a $C_5$–$C_8$ cycloalkyl radical, an aryl radical which is optionally substituted with one or more $C_1$–$C_4$ alkyl radicals; and $T_8$ is hydrogen or a methyl radical.

A first preferred family of 1,3,5-triazine derivatives is that which is, in particular, described in EP-A-0,517,104 (expressly incorporated by reference herein), and the 1,3,5-triazines having the above formula (2) while satisfying all of the following characteristics:

(i) $X_1$, $X_2$ and $X_3$ are identical and are each an oxygen atom;

(ii) $T_3$ is a $C_5$–$C_{12}$ cycloalkyl radical which is optionally substituted with one or more $C_1$–$C_4$ alkyl radicals, a radical of formula (3), (4) or (5) above in which B is a $C_1$–$C_4$ alkyl radical, and $T_8$ is the methyl radical;

(iii) $T_4$ and $T_5$, which may be identical or different, are each hydrogen, an alkali metal, an ammonium radical which is optionally substituted with one or more alkyl or hydroxyalkyl radicals, a linear or branched $C_1$–$C_{18}$ alkyl radical, a $C_5$–$C_{12}$ cycloalkyl radical which is optionally substituted with one or more $C_1$–$C_4$ alkyl radicals, or a radical of formula (3), (4) or (5) above in which B is a $C_1$–$C_4$ alkyl radical and $T_8$ is a methyl radical.

A second preferred family of 1,3,5-triazine derivatives according to the invention is that, in particular, described in EP-A-0,570,838 (also hereby expressly incorporated by reference), and the 1,3,5-triazines having the formula (2) and satisfying all of the following characteristics:

(i) $X_1$ is an oxygen atom, $X_2$ is the —NH— radical or an oxygen atom, and $X_3$ is the —NH— radical;

(ii) $T_5$ is a linear or branched $C_1$–$C_{18}$ alkyl radical, or a $C_5$–$C_{12}$ cycloalkyl radical which is optionally substituted with one or more $C_1$–$C_4$ alkyl radicals;

(ii) $T_3$ is hydrogen, an alkali metal, an ammonium radical, a radical of formula (5), a linear or branched $C_1$–$C_{18}$ alkyl radical, a $C_5$–$C_{12}$ cycloalkyl radical which is optionally substituted with one or more $C_1$–$C_4$ alkyl radicals, with the proviso that if $X_2$ is the —NH— radical, then $T_4$ is a linear or branched $C_1$–$C_{18}$ alkyl radical, or a $C_5$–$C_{12}$ cycloalkyl radical which is optionally substituted with one or more $C_1$–$C_4$ alkyl radicals; and with the further proviso that if $X_2$ is an oxygen atom, then $T_4$ is hydrogen, an alkali metal, an ammonium radical, a radical of formula (5), a linear or branched $C_1$–$C_{18}$ alkyl radical, or a $C_5$–$C_{12}$ cycloalkyl radical which is optionally substituted with one or more $C_1$–$C_4$ alkyl radicals.

A third preferred family of 1,3,5-triazine derivatives according to the invention is that, in particular, described in EP-A-0,796,851 (also expressly incorporated by reference), and the 1,3,5-triazines having the formula (2) and satisfying all of the following characteristics:

(i) $X_1$, $X_2$ and $X_3$ are each —NZ—;

(ii) the radicals Z, which may be identical or different, are each hydrogen or a linear or branched $C_1$–$C_{18}$ alkyl radical, or a $C_5$–$C_{12}$ cycloalkyl radical which may be substituted with one or more $C_1$–$C_4$ alkyl radicals;

(iii) $T_3$, $T_4$ and $T_5$, which may be identical or different, are each hydrogen or a radical Z.

These organic UV-screening agents of the triazine type are described in U.S. Pat. No. 4,617,390 and in EP-0,517,104, EP-0,570,838 and EP-0,796,851 (expressly incorporated by reference).

Exemplary UV-screening agents of the triazine type of formula (2) are, more particularly:

2,4,6-tris[p-(2'-ethylhexyl-1'-oxycarbonyl)anilino]-1,3,5-triazine which is a screening agent known per se, active in the UV-B range, existing in solid form, and which is marketed, in particular, under the trademark "UVINUL T150" by BASF this product has the following structural formula:

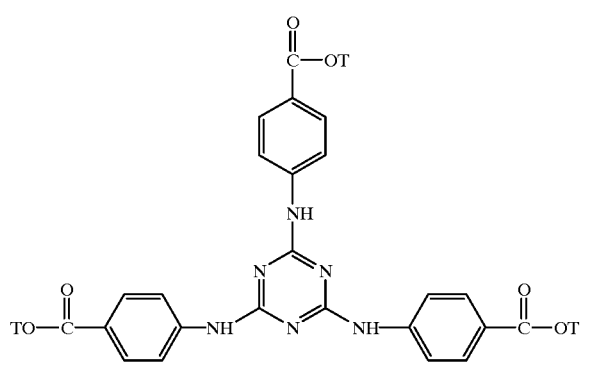

in which T is a 2-ethylhexyl radical; and

2-[(p-(tert-butylamido)anilino]-4,6-bis[(p-(2'-ethylhexyl-1'-oxycarbonyl)anilino]-1,3,5-triazine, having the following structural formula:

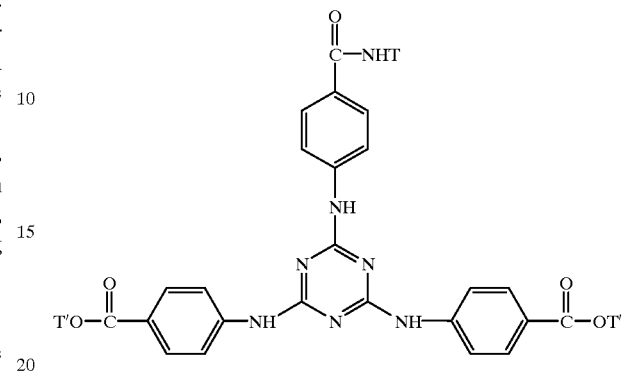

in which T' is a 2-ethylhexyl radical and T is a tert-butyl radical.

Also exemplary insoluble UV-screening agents of the triazine type in accordance with the invention are the insoluble derivatives of s-triazine substituted by benzalmalonate and/or phenylcyanoacrylate groups, such as those described in EP-A-0,790,243 (also expressly incorporated by reference).

Among these UV-screening agents of the triazine type, the following compounds are more particularly exemplary:

2,4,6-tris(diethyl 4'-aminobenzalmalonate)-s-triazine;
2,4,6-tris(diisopropyl 4'-aminobenzalmalonate)-s-triazine;
2,4,6-tris(dimethyl 4'-aminobenzalmalonate)-s-triazine;
2,4,6-tris(ethyl α-cyano-4-aminocinnamate)-s-triazine.

Among the insoluble UV-screening agents of the triazine type in accordance with the invention are those having the following structural formula (6):

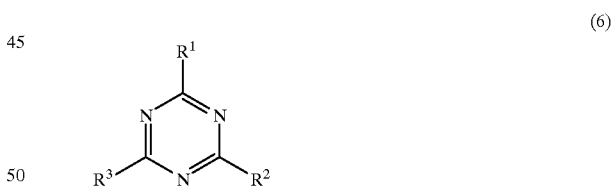

(6)

in which $R^1$, $R^2$, $R^3$ are independently phenyl, phenoxy, pyrrolo, in which the phenyl, phenoxy and pyrrolo radicals are optionally substituted with one, two or three substituents selected from among OH, $C_1$–$C_{18}$ alkyl or alkoxy, $C_1$–$C_{18}$ carboxyalkyl, $C_5$–$C_8$ cycloalkyl, a methylidenecamphor group, a group —(CH=CH)$_n$(CO)—OR$^4$, wherein $R^4$ is either $C_1$–$C_{18}$ alkyl or cinnamyl, and n is equal to 0 or 1.

These compounds are described in WO-97/03,642, GB-2,286,774, EP-0-743,309, WO-98/22,447, GB-2,319,523 (expressly incorporated by reference).

Among the insoluble UV-screening agents of the triazine type in accordance with the invention, exemplary are the insoluble derivatives of s-triazine substituted by benzotriazole and/or benzothiazole groups, such as those described in WO-98/25,922 (also expressly incorporated by reference).

More particularly exemplary are:

2,4,6-tris[(3'-benzotriazol-2-yl-2'-hydroxy-5'-methyl) phenylamino]-s-triazine; and 2,4,6-tris[(3'-benzotriazol-2-yl-2'-hydroxy-5'-ter-octyl) phenylamino]-s-triazine.

Exemplary organic UV-screening agents of the triazole type in accordance with the invention are those of the following structural formula (7) as described in WO-95/22,959 (also expressly incorporated by reference):

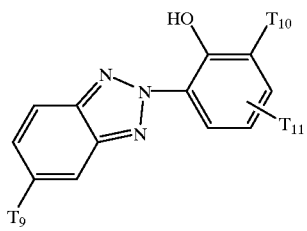

(7)

in which $T_9$ is a hydrogen atom or a $C_1$–$C_{18}$ alkyl radical; and $T_{10}$ and $T_{11}$, which may be identical or different, are each a $C_1$–$C_{18}$ alkyl radical which is optionally substituted with a phenyl radical.

Exemplary compounds of formula (7) are the commercial products TINUVIN 328, 320, 234 and 350 marketed by Ciba-Geigy having the following structural formulae:

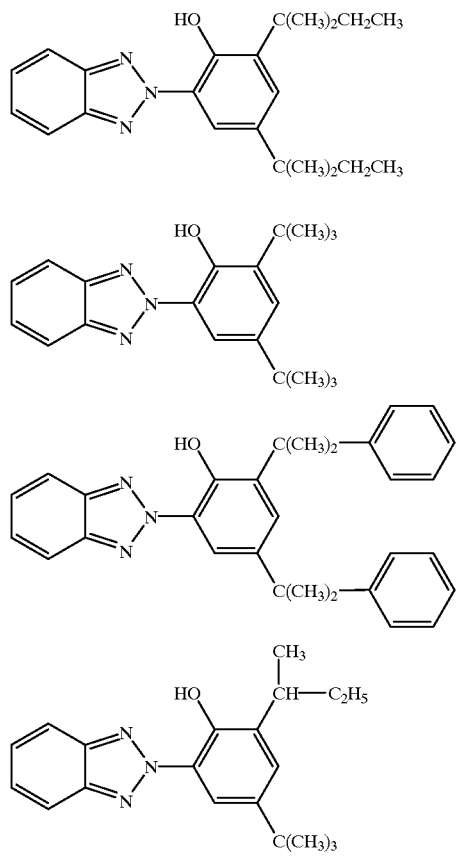

Exemplary organic UV-screening agents of the triazole type in accordance with the invention are the compounds described in U.S. Pat. Nos. 5,687,521, 5,687,521, 5,373,037, 5,362,881 and, in particular, [2,4'-dihydroxy-3-(2H-benzotriazol-2-yl)-5-(1,1,3,3-tetramethylbutyl)-2'-n-octoxy-5'-benzoyl]diphenylmethane marketed under the trademark MIXXIM. PB30 by Fairmount Chemical and having the structural formula:

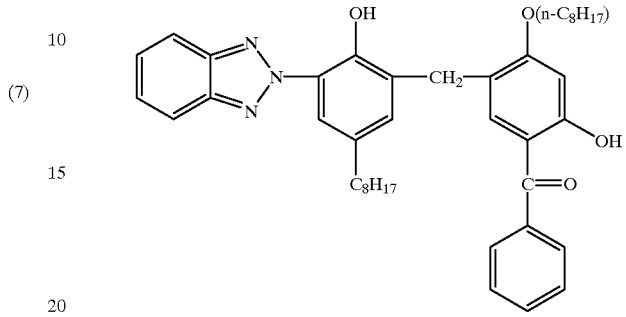

And exemplary organic UV-screening agents of the benzotriazole type in accordance with the invention are the methylenebis(hydroxyphenyl-benzotriazole) compounds having the following structural formula:

(8)

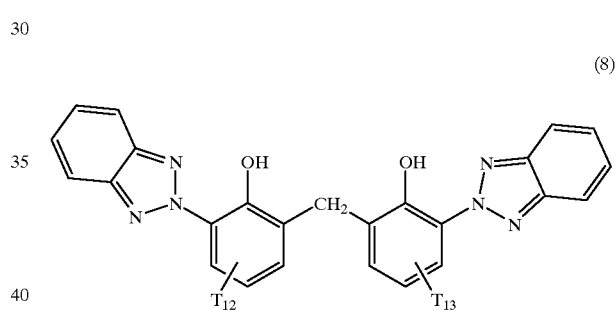

in which the radicals $T_{12}$ and $T_{13}$, which may be identical or different, are each a $C_1$–$C_{18}$ alkyl radical which may be substituted with one or more radicals selected from among a $C_1$–$C_4$ alkyl, a $C_5$–$C_{12}$ cycloalkyl, or an aryl radical. These compounds are per se known and are described in U.S. Pat. Nos. 5,237,071 and 5,166,355, GB-A-2,303,549, DE-197, 26,184 and EP-A-893,119 (also expressly incorporated by reference).

In formula (8) above, the $C_1$–$C_{18}$ alkyl radicals may be linear or branched and include, for example, methyl, ethyl, n-propyl, isopropyl, n-butyl, isobutyl, tert-butyl, tert-octyl, n-amyl, n-hexyl, n-heptyl, n-octyl, iso-octyl, n-nonyl, n-decyl, n-undecyl, n-dodecyl, tetradecyl, hexyldecyl or octadecyl; the $C_5$–$C_{12}$ cycloalkyl radicals include, for example, cyclopentyl, cyclohexyl, cyclooctyl; and the aryl radicals include, for example, phenyl or benzyl.

Among the compounds of formula (8), those having the following structural formula are particularly preferred:

compound (a)

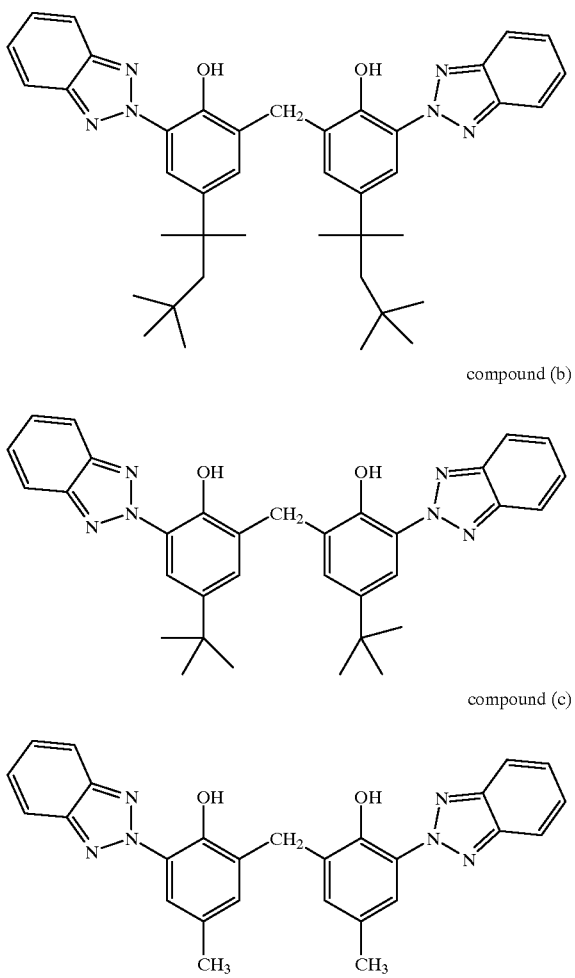

compound (b)

compound (c)

ethyl 3-octylamino-2-butenoate;
3-octylamino-1-phenyl-2-buten-1-one;
3-dodecylamino-1-phenyl-2-buten-1-one.

Exemplary insoluble organic screening agents of the cinnamamide type are those compounds described in WO-95/22,959 (expressly incorporated by reference) and having the following structural formula:

(10)

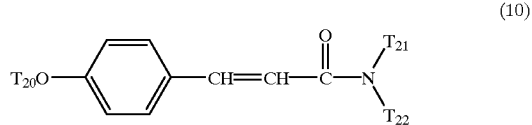

in which $T_{20}$ is a hydroxyl or $C_1$–$C_4$ alkoxy, preferably methoxy or ethoxy, radical; $T_{21}$, is hydrogen, $C_1$–$C_4$ alkyl, preferably methyl or ethyl; $T_{22}$ is a radical —(CONH)s-phenyl wherein s is equal to 0 or 1 and the phenyl group may be substituted with one, two or three groups selected from among OH, $C_1$–$C_{18}$ alkyl, $C_1$–$C_8$ alkoxy, or a radical —C(=O)—$OT_{23}$ wherein $T_{23}$ is a $C_1$–$C_{18}$ alkyl and more preferably $T_{23}$ is a phenyl, 4-methoxyphenyl or phenylaminocarbonyl group.

Also exemplary are the cinnamamide dimers such as those described in U.S. Pat. No. 5,888,481, for example, the compound having the structural formula:

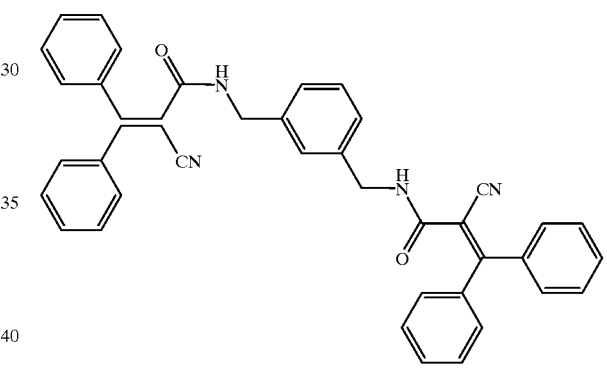

The compound (a) with the nomenclature 2,2'-methylenebis[6-(2H-benzotriazol-2-yl)-4-(1,1,3,3-tetramethylbutyl)phenol] is marketed under the trademark MJXXIM BB/100 by Fairmount Chemical. It is marketed in micronized form under the trademark TINOSORB M by Ciba-Geigy., The compound (c) with the nomenclature 2,2'-methylenebis[6-(2H-benzotriazol-2-yl)-4-(methyl)phenol] is marketed under the trademark MIXXIM BB/200 by Fairmount Chemical.

Among the organic screening agents of the vinylamide type in accordance with the invention, exemplary are the compounds of the following formulae which are described in WO-95/22,959 (expressly incorporated by reference):

$$T_{14}-(Y)r-C(=O)-C(T_{15})=C(T_{16})-N(T_{17})(T_{18}) \qquad (9)$$

in which $T_{14}$ is a $C_1$–$C_{18}$, preferably $C_1$–$C_5$, alkyl radical or a phenyl group which is optionally substituted with one, two or three radicals selected from among OH, $C_1$–$C_{18}$ alkyl, $C_1$–$C_8$ alkoxy, or a radical —C(=O)—$OT_{19}$ wherein $T_{19}$ is a $C_1$–$C_{18}$ alkyl radical; $T_{15}$, $T_{16}$, $T_{17}$ and $T_{18}$, which may be identical or different, are each a $C_1$–$C_{18}$, preferably $C_1$–$C_5$, alkyl radical or a hydrogen atom; Y is N or O and r is equal to 0 or 1.

Among these compounds, particularly representative are:
4-octylamino-3-penten-2-one;

Another specific family of insoluble organic UV-screening agents in accordance with the invention are the polyvalent metal salts (for example $Ca^{2+}$, $Zn^{2+}$, $Mg^{2+}$, $Ba^{2+}$, $Al^{3+}$ or $Zr^{4+}$) of sulfonic or carboxylic organic screening agents such as the polyvalent metal salts of sulfonated derivatives of benzylidenecamphor, for example those described in FR-A-2,639,347; the polyvalent metal salts of sulfonated derivatives of benzimidazole, for example those described in EP-A-893,119; and the polyvalent metal salts of cinnamic acid derivatives, for example those described in JP-87/166,517.

Also representative are the metal or ammonium or substituted ammonium complexes of organic UV-A and/or UV-B screening agents as described in WO-93/10,753, WO-93/11,095 and WO-95/05,150.

The micronized insoluble organic screening agent(s) according to the invention are generally present in the screening compositions according to the invention at a total concentration ranging from 0.1% and 15% by weight approximately, and preferably from 0.2% and 10% by weight approximately, relative to the total weight of the composition.

This invention also features cosmetic or dermatological compositions comprising at least one emulsion as described above.

The anti-sun cosmetic compositions according to the invention may of course contain one or more additional organic screening agents which are active in UV-A and/or UV-B ranges (absorbers), which are soluble in at least one of the phases of the subject compositions. These additional screening agents may be selected, in particular, from among the cinnamic derivatives; the dibenzoylmethane derivatives; the salicylic derivatives, the camphor derivatives; the triazine derivatives such as those described in U.S. Pat. No. 4,367,390, EP-0,863,145, EP-0,517,104, EP-0,570,838, EP-0,796,851, EP-0,775,698, EP-0,878,469 and EP-0,933,376; the benzophenone derivatives; the dimers derived from α-alkylstyrene such as those described in DE-198,55,649; the β,β'-diphenylacrylate derivatives; the benzimidazole derivatives; the bisbenzoazolyl derivatives as described in EP-A-0,669,323 and U.S. Pat. No. 2,463,264; the p-aminobenzoic acid derivatives; the polymer screening agents and silicone screening agents such as those described, in particular, in WO-93/04,665.

Exemplary such additional sunscreening agents active in the UV-A and/or UV-B ranges, which are soluble in at least one of the phases of the subject compositions, include:
p-aminobenzoic acid;
oxyethylenated p-aminobenzoate (25 mol);
2-ethylhexyl p-dimethylaminobenzoate;
N-oxypropylenated ethyl p-aminobenzoate;
glyceryl p-aminobenzoate;
homomenthyl salicylate;
2-ethylhexyl salicylate;
triethanolamine salicylate;
4-isopropylbenzyl salicylate;
4-tert-butyl-4'-methoxydibenzoylmethane;
4-isopropyl-dibenzoylmethane;
2-ethylhexyl 4-methoxycinnamate;
methyl diisopropylcinnamate;
isoamyl 4-methoxycinnamate;
diethanolamine 4-methoxycinnamate;
menthyl anthranilate;
2-ethylhexyl-2-cyano-3,3'-diphenylacrylate;
ethyl 2-cyano-3,3'-diphenylacrylate;
2-phenylbenzimidazole-5-sulfonic acid and salts thereof;
3-(4'-trimethylammonium)benzylidenebornan-2-one methyl sulfate;
2-hydroxy-4-methoxybenzophenone;
2-hydroxy-4-methoxybenzophenone-5-sulfonate;
2,4-dihydroxybenzophenone;
2,2'-4,4'-tetrahydroxybenzophenone;
2,2'-dihydroxy-4,4'-dimethoxybenzophenone;
2-hydroxy-4-n-octoxybenzophenone;
2-hydroxy-4-methoxy-4'-methylbenzophenone;
a-(2-oxoborn-3-ylidene)tolyl-4-sulfonic acid and its soluble salts;
3-(4'-sulfo)benzylidenebornan-2-one and its soluble salts;
3-(4'-methylbenzylidene)-d,1-camphor;
3-benzylidene-d,1-camphor;
1,4-benzene[di(3-methylidene-10-camphorsulfonic)] acid and its soluble salts;
urocanic acid;
2,4-bis{[4-2-ethylhexyloxy)]-2-hydroxy]phenyl}-6-(4-methoxyphenyl)-1,3,5-triazine;
the polymer of N-(2 and 4)-[(2-oxoborn-3-ylidene)methyl] benzyl]acrylamide;
1,4-bisbenzimidazolylphenylene-3,3',5,5'-tetrasulfonic acid and its soluble salts;
polyorganosiloxanes containing a benzalmalonate function;
polyorganosiloxanes containing a benzotriazole function such as Drometrizole Trisiloxane.

The compositions according to the invention may also contain agents for tanning and/or for artificial tanning of the skin (self-tanning agents), such as, for example, dihydroxyacetone (DHA).

The cosmetic compositions according to the invention may also contain pigments or, alternatively, nanopigments (mean size of the primary particles: generally ranging from 5 nm to 100 nm, preferably from 10 nm to 50 nm) of metal oxides, coated or uncoated, such as, for example, nanopigments of titanium dioxide (amorphous or crystallized in the rutile and/or anatase state), of iron oxide, zinc oxide, zirconium oxide or cerium oxide, which are all UV photoprotective agents well known per se. Conventional coating agents are moreover alumina and/or aluminum stearate. Such nanopigments of metal oxides, coated or uncoated, are, in particular, described in EP-A-0,518,772 and EP-A-0,518,773.

The compositions of the invention may comprise, in addition, conventional cosmetic additives and adjuvants selected, in particular, from among fatty substances, organic solvents, thickeners, demulcents, opacifiers, colorants, stabilizers, emollients, antifoaming agents, moisturizing agents, perfumes, preservatives, polymers, fillers, sequestrants, propellants, alkalinizing or acidifying agents or any other ingredient customarily formulated into cosmetics, in particular for the production of anti-sun/sunscreen compositions in the form of emulsions.

The fatty substances may be an oil or a wax or mixtures thereof, and they also comprise fatty acids, fatty alcohols and esters of fatty acids. The oils may be selected from among animal, vegetable, mineral or synthetic oils and, in particular, from among liquid paraffin, paraffin oil, silicone oils, volatile or otherwise, isoparaffins, polyolefins, fluorinated or perfluorinated oils. Likewise, the waxes may be animal, fossil, vegetable, mineral or synthetic waxes which are also known per se.

Exemplary organic solvents include the lower alcohols and polyols.

Of course, one skilled in this art will take care to select this or these optional additional compounds and/or their quantities such that the advantageous properties, in particular the resistance to water, the stability, which are intrinsically associated with the emulsions in accordance with the invention are not, or not substantially, altered by the addition(s) envisaged.

The compositions of the invention may be formulated according to techniques well known to this art, in particular those suited for the preparation of emulsions of the oil-in-water or water-in-oil type.

The subject compositions may be provided, in particular, in the form of a simple or complex (O/W, W/O, O/W/O or W/O/W) emulsion such as a cream, a milk, a gel or a gel cream, of a powder, a lotion, an ointment, a solid stick and may optionally be packaged as an aerosol and provided in the form of a foam, mousse or spray.

When an emulsion is provided, the aqueous phase thereof may comprise a nonionic vesicular dispersion prepared according to known techniques (Bangham, Standish and Watkins, *J. Mol. Biol.*, 13, 238 (1965), FR-2,315,991 and FR-2,416,008).

The cosmetic compositions according to the invention may be formulated for protecting the human epidermis or the hair against the damaging effects of ultraviolet radiation, as an anti-sun composition or as a makeup product.

When the cosmetic compositions according to the invention are formulated for protecting the human epidermis against UV rays, or as anti-sun/sunscreen compositions, same may be provided in the form of a suspension or a dispersion in solvents or fatty substances, in the form of a nonionic vesicular dispersion or, alternatively, in the form of an emulsion, preferably of the oil-in-water type, such as a cream or a milk, in the form of an ointment, a gel, a gel cream, a solid stick, a powder, a stick, an aerosol foam or a spray.

When the cosmetic compositions according to the invention are formulated for protecting the hair against UV rays, same may be provided in the form of a shampoo, a lotion, a gel, an emulsion, a nonionic vesicular dispersion and may constitute, for example, a rinse-off composition to be applied before or after shampooing, before or after dyeing or bleaching, before, during or after permanent-waving or hair straightening, a hair-styling or treatment lotion or gel, a lotion or gel for blow drying or hair setting, a composition for permanent waving or straightening, dyeing or bleaching the hair.

When the subject compositions are formulated as makeup products for the eyelashes, the eyebrows or the skin, such as a treatment cream for the epidermis, foundation, lipstick, eyeshadow, blusher, mascara or eyeliner, same may be provided in a solid or pasty, anhydrous or aqueous form, such as oil-in-water or water-in-oil emulsions, nonionic vesicular dispersions or alternatively suspensions.

For example, for the anti-sun formulations in accordance with the invention which have a carrier, vehicle or diluent of the oil-in-water emulsion type, the aqueous phase (comprising in particular the hydrophilic screening agents), generally constitutes from 50% to 95% by weight, preferably from 70% to 90% by weight, relative to the total weight of the formulation, the oily phase (comprising in particular the lipophilic screening agents), from 5% to 50% by weight, preferably from 10% to 30% by weight, relative to the total weight of the formulation, and the (co)emulsifier(s) from 0.5% to 20% by weight, preferably from 2% to 10% by weight, also relative to the total weight of the formulation.

As indicated above, the present invention thus features formulating the subject emulsions for the production of cosmetic compositions for protecting the skin and/or the hair against ultraviolet radiation, in particular solar radiation.

This invention also features formulating photoprotective cosmetic or dermatological emulsions without employing any emulsifying agent(s), the subject emulsion containing at least one organic UV-screening agent insoluble therein, for increasing the water resistance of its screening power (stability to water).

In order to further illustrate the present invention and the advantages thereof, the following specific examples of formulations are given, it being understood that same are intended only as illustrative and in nowise limitative.

EXAMPLE 1

| COMPOSITION | |
|---|---|
| $C_{12}/C_{15}$ alcohol benzoate (WITCONOL TN - WITCO) | 10 g |
| Methylenebis(tetramethylbutylhydroxyphenylbenzotriazole) in micronized insoluble form marketed under the trademark TINOSORB M by CIBA GEIGY - mean particle size 0.15–0.2 μm | 2.5 g |
| Octocrylene (UVINUL N539-BASF) | 5 g |
| 4-tert-butyl-4'-methoxydibenzoylmethanol (PARSOL 1789-HOFFMANN LAROCHE) | 2 g |

| -continued | |
|---|---|
| COMPOSITION | |
| Crosslinked acrylic acid/($C_{10}$–$C_{30}$) alkyl acrylate copolymer (PEMULEN TR1-GOODRICH) | 0.75 g |
| Titanium dioxide (TITANIUM DIOXYDE MT 100 TV TAYCA) | 3 g |
| EDTA | 0.1 g |
| 1,4-benzene[di(3-methylidene-10-camphorsulfonic)] acid (MEXORYL SX-CHIMEX) | 0.5 g |
| Glycerin | 5 g |
| Triethanolamine, preservatives pH = 7 | qs |
| Demineralized water qs | 100 g |

EXAMPLE 2

| COMPOSITION | |
|---|---|
| $C_{12}/C_{15}$ alcohol benzoate (WITCONOL TN - WITCO) | 8 g |
| Methylenebis(tetramethylbutylhydroxyphenylbenzotriazole) in micronized insoluble form marketed under the trademark TINOSORB M by CIBA GEIGY - mean particle size 0.15–0.2 μm | 3 g |
| Octocrylene (UVINUL N539-BASF) | 5 g |
| 2,4-bis{[(4-2-ethylhexyloxy)]-2-hydroxy]phenyl}-6-(4-methoxyphenyl)-1,3,5-triazine | 3 g |
| Crosslinked methacrylic acid/ethyl acrylate/steareth 10 allyl ether terpolymer in aqueous emulsion (SALCARE-SC90-ALLIED COLLOIDS) | 5 g |
| Titanium dioxide (TITANIUM DIOXYDE MT 100 TV TAYCA) | 3 g |
| Glycerin | 5 g |
| Triethanolamine, preservatives | qs pH = 7 |
| Demineralized water qs | 100 g |

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A topically applicable, water-resistant but emulsifier-free UV-photoprotecting cosmetic/dermatological emulsion comprising (a) at least one aqueous phase and (b) at least one fatty phase, (c) an effective UV-photoprotecting amount of at least one micronized organic UV-screening agent insoluble therein, the mean particle size of said micronized particles ranging from 0.01 to 2 μm and (d) optionally, at least one crosslinked polymer of at least one ethylenically unsaturated monomer.

2. The topically applicable UV-photoprotecting emulsion as defined by claim 1, the mean particle size of said micronized particles ranging from 0.02 to 1.5 μm.

3. The topically applicable UV-photoprotecting emulsion as defined by claim 2, the mean particle size of said micronized particles ranging from 0.03 to 1.0 μm.

4. The topically applicable UV-photoprotecting emulsion as defined by claim 1, said micronized particles having been formed by grinding course particulates of said insoluble organic UV-screening agent in the presence of a surfactant.

5. The topically applicable UV-photoprotecting emulsion as defined by claim 4, said surfactant comprising an alkyl polyglucoside having the formula $C_nH_{2n+1}O(C_6H_{10}O_5)_xH$ in which n is an integer ranging from 8 to 16 and x is the average degree of polymerization of the structural unit $(C_6H_{10}O_5)$ and varies from 1.4 to 1.6.

6. The topically applicable UV-photoprotecting emulsion as defined by claim 4, said surfactant being present at a concentration ranging from 1% to 50% by weight relative to the insoluble organic UV-screening agent in its micronized state.

7. The topically applicable UV-photoprotecting emulsion as defined by claim 1, comprising (d) at least one crosslinked polymer of at least one ethylenically unsaturated monomer selected from the group consisting of:
  (i) a crosslinked homopolymer or copolymer of at least one ethylenically unsaturated monomer having a sulfonic functional group, in free or partially or completely salified form;
  (ii) a crosslinked copolymer of at least one ethylenically unsaturated monomer having a carboxylic acid functional group, in free or partially or completely salified form, or of an ester or amide derivative thereof;
  (iii) a crosslinked homopolymer or copolymer of at least one cationic ethylenically unsaturated ester or amide monomer.

8. The topically applicable UV-photoprotecting emulsion as defined by claim 7, comprising at least one crosslinked homopolymer of 2-acrylamido-2-methylpropanesulfonic acid that is at least 90% neutralized, and/or at least one crosslinked copolymer of 2-acrylamido-2-methylpropanesulfonic acid and of acrylamide that is partially or completely neutralized.

9. The topically applicable UV-photoprotecting emulsion as defined by claim 7, comprising at least one non-ionic or anionic crosslinked amphiphilic polymer containing at least one fatty chain or substituent and at least one hydrophilic structural unit.

10. The topically applicable UV-photoprotecting emulsion as defined by claim 9, comprising at least one crosslinked copolymer of $C_1$–$C_6$ alkyl methacrylates or acrylates and of amphiphilic monomers containing at least one fatty chain or substituent, and/or at least one crosslinked copolymer of hydrophilic methacrylates or acrylates and of hydrophobic monomers containing at least one fatty chain.

11. The topically applicable UV-photoprotecting emulsion as defined by claim 9, comprising at least one anionic crosslinked amphiphilic polymer of an ethylenically unsaturated hydrophobic anionic monomer.

12. The topically applicable UV-photoprotecting emulsion as defined by claim 9, comprising at least one anionic crosslinked amphiphilic polymer of acrylic acid, methacrylic acid or mixture thereof and also of a fatty hydrophobic monomer having the following formula (I):

$$CH_2=C(R')CH_2OB_nR \quad (1)$$

in which R' is H or $CH_3$, B represents the ethyleneoxy radical, n is zero or an integer ranging from 1 to 100, and R is an alkyl, arylalkyl, aryl, alkylaryl or cycloalkyl radical having from 8 to 30 carbon atoms.

13. The topically applicable UV-photoprotecting emulsion as defined by claim 12, wherein in formula (I), R' is H, n is equal to 10, and R is a stearyl ($C_{18}$) radical.

14. The topically applicable UV-photoprotecting emulsion as defined by claim 12, comprising at least one anionic crosslinked amphiphilic polymer of 20% to 60% by weight of acrylic acid and/or methacrylic acid, of 5% to 60% by weight of lower alkyl (meth)acrylates, of 2% to 50% by weight of a fatty allyl ether of formula (I), and of up to 1% by weight of a crosslinking agent.

15. The topically applicable UV-photoprotecting emulsion as defined by claim 12, comprising at least one anionic crosslinked amphiphilic terpolymer of methacrylic acid, ethyl acrylate, polyethylene glycol (10 EO) stearyl alcohol ether (steareth 10).

16. The topically applicable UV-photoprotecting emulsion as defined by claim 11, comprising at least one anionic crosslinked amphiphilic polymer of at least one olefinically unsaturated hydrophilic carboxylic acid monomer and of at least one hydrophobic ($C_{10}$–$C_{30}$) alkyl ester of an unsaturated carboxylic acid.

17. The topically applicable UV-photoprotecting emulsion as defined by claim 16, comprising at least one amphiphilic crosslinked polymer of a hydrophilic olefinically unsaturated carboxylic acid monomer having the following formula (II):

in which $R^1$ is H or $CH_3$ or $C_2H_5$, and of a hydrophobic ($C_{10}$–$C_{30}$) alkyl ester of an unsaturated carboxylic acid having the following formula (III):

in which $R^1$ is H or $CH_3$ or $C_2H_5$, and $R^2$ is a $C_{10}$–$C_{30}$ alkyl radical.

18. The topically applicable UV-photoprotecting emulsion as defined by claim 7, comprising at least one crosslinked hompolymer of ammonium acrylate or copolymer of ammonium acrylate and of acrylamide, and/or at least one crosslinked homopolymer of dimethylaminoethyl methacrylate quaternized with methyl chloride or the copolymer of dimethylaminoethyl methacrylate quaternized with methyl chloride.

19. The topically applicable UV-photoprotecting emulsion as defined by claim 7, comprising from 0.01% to 10% by weight of said at least one crosslinked polymer.

20. The topically applicable UV-photoprotecting emulsion as defined by claim 1, said at least one insoluble organic UV-screening agent comprising an oxanilide, triazine, triazole, vinylamide, or cinnamide.

21. The topically applicable UV-photoprotecting emulsion as defined by claim 20, said at least one insoluble organic UV-screening agent comprising an oxanilide having the structural formula (1):

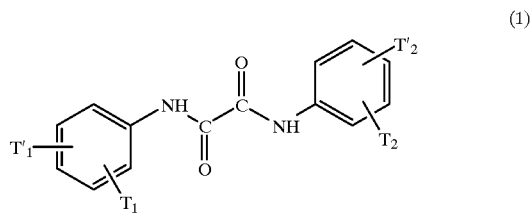

in which $T_1$, $T'_1$, $T_2$ and $T'_2$, which may be identical or different, are each a $C_1$–$C_8$ alkyl radical or a $C_1$–$C_8$ alkoxy radical.

22. The topically applicable UV-photoprotecting emulsion as defined by claim 20, said at least one insoluble organic UV-screening agent comprising a triazine having the structural formula (2):

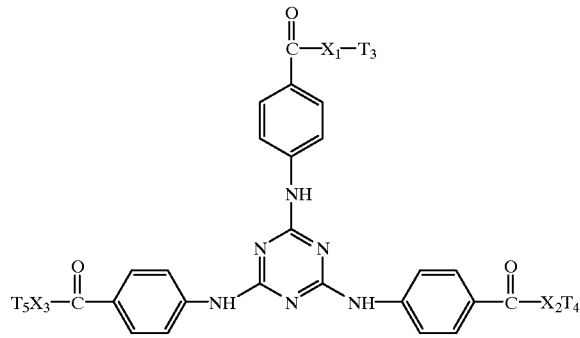

(2)

in which $X_1$, $X_2$ and $X_3$, which may be identical or different, are each an oxygen atom or a radical —NZ—; the radicals Z, which may be identical or different, are each hydrogen or a linear or branched $C_1$–$C_{18}$ alkyl radical, a $C_5$–$C_{12}$ cycloalkyl radical which may be substituted with one or more $C_1$–$C_4$ alkyl radicals; $T_3$, $T_4$ and $T_5$, which may be identical or different, are each hydrogen, an alkali metal, an ammonium radical which is optionally substituted with one or more alkyl or hydroxyalkyl radicals, a linear or branched $C_1$–$C_{18}$ alkyl radical, a $C_5$–$C_{12}$ cycloalkyl radical which is optionally substituted with one or more $C_1$–$C_4$ alkyl radicals, a polyoxyethylenated radical containing from 1 to 6 ethylene oxide units and whose terminal OH group is methylated, or a radical of the following formula (3), (4) or (5):

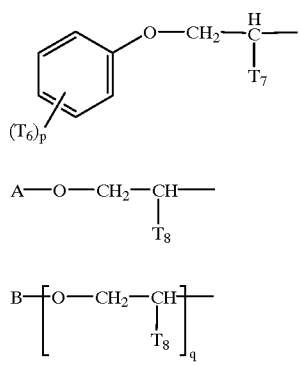

(3)

A—O—CH$_2$—CH—
         |
         T$_8$ (4)

B—[O—CH$_2$—CH]—
              |
              T$_8$  $_q$ (5)

wherein $T_6$ is hydrogen or a methyl radical; $T_7$ is a $C_1$–$C_9$ alkyl radical; p is an integer ranging from 0 to 3; q is an integer ranging from 1 to 10; A is a $C_4$–$C_8$ alkyl radical or a $C_5$–$C_8$ cycloalkyl radical; B is a linear or branched $C_1$–$C_8$ alkyl radical, a $C_5$–$C_8$ cycloalkyl radical, or an aryl radical which is optionally substituted with one or more $C_1$–$C_4$ alkyl radicals; and $T_8$ is hydrogen or a methyl radical.

23. The topically applicable UV-photoprotecting emulsion as defined by claim 22, said triazine UV-screening agent having the following structural formula:

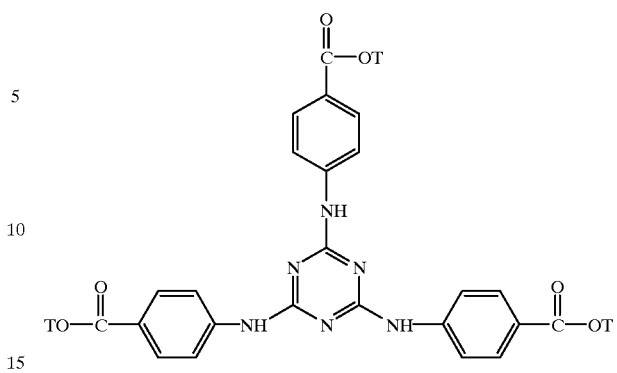

in which T is a 2-ethylhexyl radical.

24. The topically applicable UV-photoprotecting emulsion as defined by claim 22, said triazine UV-screening agent having the following structural formula:

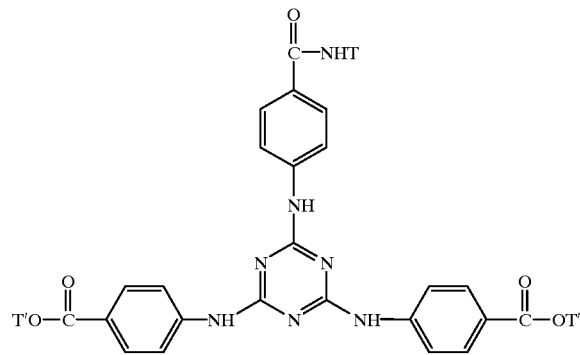

in which T' is a 2-ethylhexyl radical and T is a tert-butyl radical.

25. The topically applicable UV-photoprotecting emulsion as defined by claim 20, said at least one organic UV-screening agent comprising an insoluble s-triazine bearing benzalmalonate and/or phenylcyanoacrylate substituents.

26. The topically applicable UV-photoprotecting emulsion as defined by claim 25, said at least one triazine UV-screening agent comprising 2,4,6-tris(diethyl 4'-aminobenzalmalonate)-s-triazine; 2,4,6-tris(diisopropyl 4'-aminobenzalmalonate)-s-triazine; 2,4,6-tris(dimethyl 4'-arninobenzalmalonate)-s-triazine or 2,4,6-tris(ethyl a-cyano-4-aminocinnamate)-s-triazine.

27. The topically applicable UV-photoprotecting emulsion as defined by claim 20, said at least one insoluble-organic UV-screening agent comprising a triazine having the following structural formula:

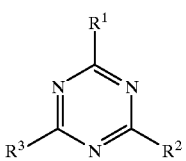

(6)

in which $R^1$, $R^2$, $R^3$ are independently phenyl, phenoxy, or pyrrolo radicals, optionally substituted with one, two or three substituents selected from among OH, $C_1$–$C_{18}$ alkyl or alkoxy, $C_1$–$C_{18}$ carboxyalkyl, $C_5$–$C_8$ cycloalkyl, a methylidenecamphor group, a radical —(CH=CH)$_n$(CO)—OR$^4$, wherein R$^4$ is C$_1$–C$_{18}$ alkyl or cinnamyl, and n is equal to 0 or 1.

28. The topically applicable UV-photoprotecting emulsion as defined by claim 20, said at least one organic UV-screening agent comprising an s-triazine bearing benzotriazole and/or benzothiazole substituents.

29. The topically applicable UV-photoprotecting emulsion as defined by claim 20, said at least one insoluble triazine UV-screening agent comprising 2,4,6-tris[(3'-benzotriazol-2-yl-2'-hydroxy-5'-methyl)phenylamino]-s-triazine, or 2,4,6-tris[(3'-benzotriazol-2-yl-2'-hydroxy-5'-ter-octyl)phenylamino]-s-triazine.

30. The topically applicable UV-photoprotecting emulsion as defined by claim 20, said at least one insoluble organic UV-screening agent comprising a triazole having the following structural formula (7):

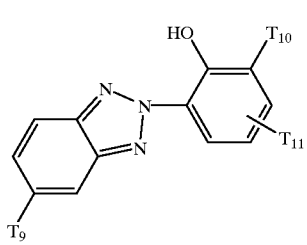

(7)

in which T$_9$ is a hydrogen atom or a C$_1$–C$_{18}$ alkyl radical; and T$_{10}$ and T$_{11}$, which may be identical or different, are each a C$_1$–C$_{18}$ alkyl radical which is optionally substituted with a phenyl radical.

31. The topically applicable UV-photoprotecting emulsion as defined by claim 30, said compound of formula (7) being selected from among:

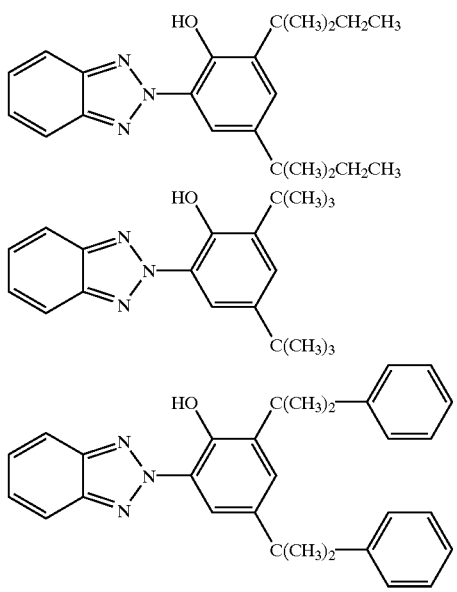

32. The topically applicable UV-photoprotecting emulsion as defined by claim 20, said at least one insoluble organic UV-screening agent comprising [2,4'-dihydroxy-3-(2H-benzotriazol-2-yl)-5-(1,1,3,3-tetramethylbutyl)-2'-n-octoxy-5'-benzoyl]diphenylmethane having the structural formula:

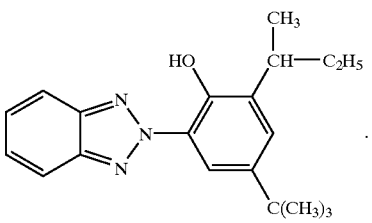

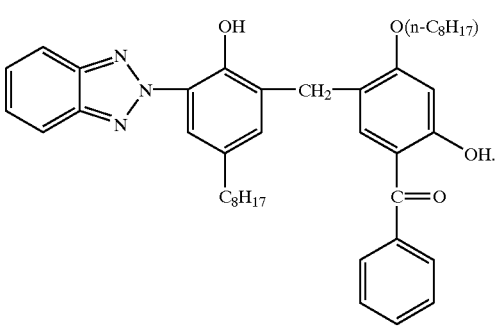

33. The topically applicable UV-photoprotecting emulsion as defined by claim 20, said at least-one insoluble organic UV-screening agent comprising a methylenebis (hydroxyphenylbenzo-triazole) having the following structural formula:

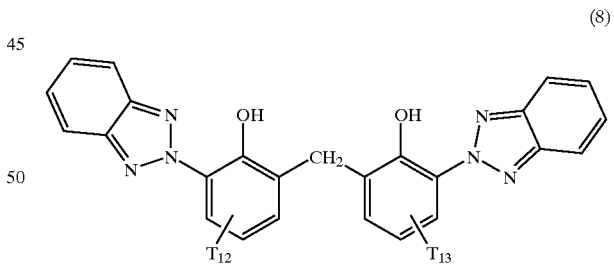

(8)

in which the radicals T$_{12}$ and T$_{13}$, which may be identical or different, are each a C$_1$–C$_{18}$ alkyl radical optionally substituted with one or more C$_1$–C$_4$ alkyl, C$_5$–C$_{12}$ cycloalkyl, or aryl radicals.

34. The topically applicable UV-photoprotecting emulsion as defined by claim 33, said compound of formula (8) being selected from among:

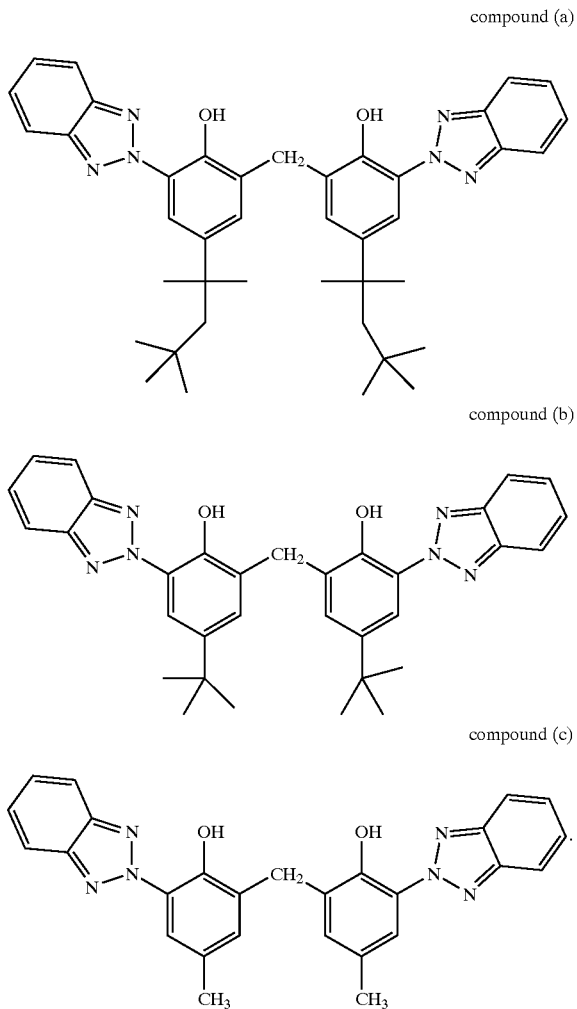

compound (a)

compound (b)

compound (c)

35. The topically applicable UV-photoprotecting emulsion as defined by claim 20, said at least one insoluble organic UV-screening agent comprising a vinylamide having the following structural formula:

$$T_{14}—(Y)r\text{-}C(=O)—C(T_{15})=C(T_{16})—N(T_{17})(T_{18}) \tag{9}$$

in which $T_{14}$ is a $C_1$–$C_{18}$ alkyl radical or a phenyl radical which is optionally substituted with one, two or three radicals selected from among OH, $C_1$–$C_{18}$ alkyl, $C_1$–$C_8$ alkoxy, or a radical —C(=O)—$OT_{19}$ wherein $T_{19}$ is a $C_1$–$C_{18}$ alkyl radical; $T_{15}$, $T_{16}$, $T_{17}$ and $T_{18}$, which may be identical or different, are each a $C_1$–$C_{18}$ alkyl radical or a hydrogen atom; Y is N or O and r is equal to 0 or 1.

36. The topically applicable UV-photoprotecting emulsion as defined by claim 35, said compound of formula (9) comprising 4-octylamino-3-penten-2-one; ethyl 3-octylamino-2-butenoate; 3-octylamino-1-phenyl-2-buten-1-one; or 3-dodecylamino-1-phenyl-2-buten-1-one.

37. The topically applicable UV-photoprotecting emulsion as defined by claim 20, said at least one insoluble organic UV-screening agent comprising a cinnamamide having the following structural formula:

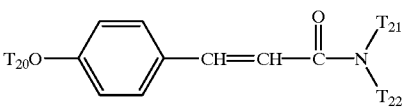

in which $OT_{20}$ is a hydroxyl or $C_1$–$C_4$ alkoxy radical; $T_{21}$ is hydrogen or $C_1$–$C_4$ alkyl; $T_{22}$ is a radical —(CONH)s-phenyl wherein s is equal to 0 or 1 and the phenyl group may be substituted with one, two or three groups selected from among OH, $C_1$–$C_{18}$ alkyl, $C_1$–$C_8$ alkoxy, or a radical —C(=O)—$OT_{23}$ wherein $T_{23}$ is a $C_1$–$C_{18}$ alkyl, phenyl, 4-methoxyphenyl or phenylaminocarbonyl group.

38. The topically applicable UV-photoprotecting emulsion as defined by claim 20, said at least one insoluble organic UV-screening agent comprising a cinnamamide dimer.

39. The topically applicable UV-photoprotecting emulsion as defined by claim 38, said insoluble organic UV-screening agent having the structural formula:

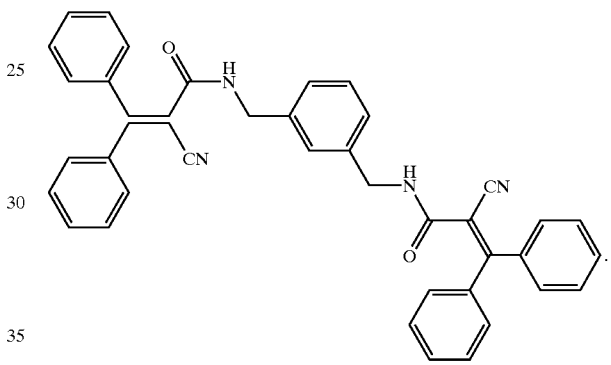

40. The topically applicable UV-photoprotecting emulsion as defined by claim 1, said at least one insoluble organic UV-screening agent comprising a polyvalent metal salt of a sulfonic or carboxylic organic screening agent.

41. The topically applicable UV-photoprotecting emulsion as defined by claim 40, said at least one insoluble organic UV-screening agent comprising a polyvalent metal salt of a sulfonated derivative of benzylidenecamphor, a polyvalent metal salt of a sulfonated derivative of benzimidazole, or a polyvalent metal salt of a derivative of cinnamic acid.

42. The topically applicable UV-photoprotecting emulsion as defined by claim 1, said at least one insoluble organic UV-screening agent comprising a complex of a polyvalent metal or of ammonium with organic UV-A and/or UV-B screening agents.

43. The topically applicable UV-photoprotecting emulsion as defined by claim 1, formulated into a cosmetically/dermatologically acceptable vehicle, diluent or carrier therefor.

44. The topically applicable UV-photoprotecting emulsion as defined by claim 1, further comprising one or more additional organic screening agents active in UV-A and/or UV-B range, soluble in one of the phases thereof.

45. The topically applicable UV-photoprotecting emulsion as defined by claim 44, said one or more additional organic screening agents being selected from among cinnamic derivatives; salicylic derivatives; camphor derivatives; triazine derivatives; dibenzoyl-methane derivatives; benzophenone derivatives; β, β'-diphenyl acrylate derivatives; benzimidazole derivatives; dimers of α-alkylstyrene; bisbenzoazolyl derivatives; p-aminobenzoic acid derivatives; polymer screening agents and silicone screening agents.

46. The topically applicable UV-photoprotecting emulsion as defined by claim 1, further comprising coated or uncoated pigments or nanopigments of metal oxides.

47. The topically applicable UV-photoprotecting emulsion as defined by claim 46, further comprising pigments or nanopigments of titanium, zinc, iron, zirconium or cerium oxides, or mixtures thereof.

48. The topically applicable UV-photoprotecting emulsion as defined by claim 1, further comprising at least one agent for tanning and/or for artificial tanning of the skin.

49. The topically applicable UV-photoprotecting emulsion as defined by claim 1, further comprising at least one fatty substance, organic solvent, thickener, demulcent, opacifier, stabilizer, emollient, anti-foaming agent, moisturizing agent, perfume, preservative, colorant, polymer, filler, sequestrant, propellant, alkalinizing or acidifying agent, or combination thereof.

50. The topically applicable UV-photoprotecting emulsion as defined by claim 1, formulated as a nonionic vesicular dispersion, a cream, a milk, a gel, a lotion, an ointment, a gel cream, a suspension, a dispersion, a powder, a shampoo, a solid stick, a foam or a spray.

51. The topically applicable UV-photoprotecting emulsion as defined by claim 1, formulated as a makeup composition for the eyelashes, the eyebrows or the skin and being in solid or pasty, anhydrous or aqueous form, or in the form of a suspension or a dispersion.

52. A method or regime/regimen for photoprotecting human skin and/or hair against the deleterious effects of ultraviolet radiation, comprising topically applying thereto an effective amount of the UV-photoprotecting cosmetic/dermatological emulsion as defined by claim 1.

53. A method or regime/regimen for photoprotecting human skin and/or hair against the deleterious effects of solar radiation, comprising topically applying thereto an effective amount of the UV-photoprotecting cosmetic/dermatological emulsion as defined by claim 1.

* * * * *